(12) United States Patent
Austin et al.

(10) Patent No.: US 11,712,322 B2
(45) Date of Patent: Aug. 1, 2023

(54) HOUSING ASSEMBLY FOR PERIODONTAL ENDOSCOPIC PROBE

(71) Applicant: PERIOENDOSCOPY, LLC, Scottsdale, AZ (US)

(72) Inventors: Michael D. Austin, Scottsdale, AZ (US); Chad E. Kennedy, Gilbert, AZ (US)

(73) Assignee: PPE-AZ, LLC, Scottsdale, AZ (US)

( * ) Notice: Subject to any disclaimer, the term of this patent is extended or adjusted under 35 U.S.C. 154(b) by 910 days.

(21) Appl. No.: 16/623,236

(22) PCT Filed: Sep. 11, 2017

(86) PCT No.: PCT/US2017/050971
§ 371 (c)(1),
(2) Date: Dec. 16, 2019

(87) PCT Pub. No.: WO2018/049332
PCT Pub. Date: Mar. 15, 2018

(65) Prior Publication Data
US 2020/0345211 A1 Nov. 5, 2020

Related U.S. Application Data

(60) Provisional application No. 62/393,085, filed on Oct. 14, 2016, provisional application No. 62/393,082, filed on Sep. 11, 2016.

(51) Int. Cl.
*A61C 1/08* (2006.01)
*A61B 1/00* (2006.01)
(Continued)

(52) U.S. Cl.
CPC .............. *A61C 1/08* (2013.01); *A61B 1/0052* (2013.01); *A61B 1/00068* (2013.01);
(Continued)

(58) Field of Classification Search
CPC ........... A61C 1/08; A61C 1/082; A61C 1/084; A61C 1/085; A61C 1/088; A61C 1/14;
(Continued)

(56) References Cited

U.S. PATENT DOCUMENTS

| 4,561,845 A | 12/1985 | Meller |
| 5,897,509 A | 4/1999 | Toda |

(Continued)

FOREIGN PATENT DOCUMENTS

| JP | 2012239726 | 12/2012 |
| JP | 2012239727 | 12/2012 |

*Primary Examiner* — Ryan N Henderson
(74) *Attorney, Agent, or Firm* — Bycer & Marion, PLC; Matthew L. Bycer

(57) ABSTRACT

An assembly for aiding field use of an endoscopic probe is disclosed. The assembly includes a housing assembly for an endoscopic probe and a compatible holder for the housing assembly. The housing assembly includes a tubular conduit for receiving the endoscopic probe and a plug coupled along a distal end of the tubular conduit. The holder includes a pre-configured arm for facilitating an exploration of a pre-determined quadrant of an oral cavity. The explorer includes a plug receiver. Upon coupling the plug receiver with the inversely matching plug, the tubular conduit passes through the opening and into the third axial channel.

19 Claims, 13 Drawing Sheets

(51) Int. Cl.
*A61B 1/005* (2006.01)
*A61B 1/24* (2006.01)

(52) U.S. Cl.
CPC ...... *A61B 1/00119* (2013.01); *A61B 1/00121* (2013.01); *A61B 1/00135* (2013.01); *A61B 1/00147* (2013.01); *A61B 1/24* (2013.01)

(58) Field of Classification Search
CPC ......... A61C 1/141; A61C 1/142; A61C 1/144; A61C 1/145; A61C 1/147; A61C 1/148; A61C 3/04; A61B 1/00066; A61B 1/00112; A61B 1/00114; A61B 1/00117; A61B 1/00119; A61B 1/00121; A61B 1/00124; A61B 1/00126; A61B 1/00128; A61B 1/00135; A61B 1/00142; A61B 1/00154; A61B 1/00147; A61B 1/00149; A61B 1/24; A61B 1/313; A61B 1/3132; A61B 1/3135; A61B 1/3137; A61B 1/317
See application file for complete search history.

(56) References Cited

U.S. PATENT DOCUMENTS

| | | | |
|---|---|---|---|
| 5,944,520 A | 8/1999 | Ash | |
| 8,585,402 B2* | 11/2013 | Vogel | A61C 1/084 433/72 |
| 8,708,699 B2* | 4/2014 | Suter | A61C 1/084 433/75 |
| 9,610,137 B1* | 4/2017 | Kris | A61C 1/088 |
| 9,930,294 B2* | 3/2018 | Hasegawa | H04N 23/51 |
| 11,033,366 B2* | 6/2021 | Mozes | G16H 20/40 |
| 2002/0147394 A1 | 10/2002 | Ellingsen | |
| 2006/0063973 A1 | 3/2006 | Makower | |
| 2007/0213647 A1 | 9/2007 | Incardona | |
| 2010/0254149 A1 | 10/2010 | Gill | |
| 2017/0209154 A1* | 7/2017 | Krause | A61B 17/8875 |

* cited by examiner

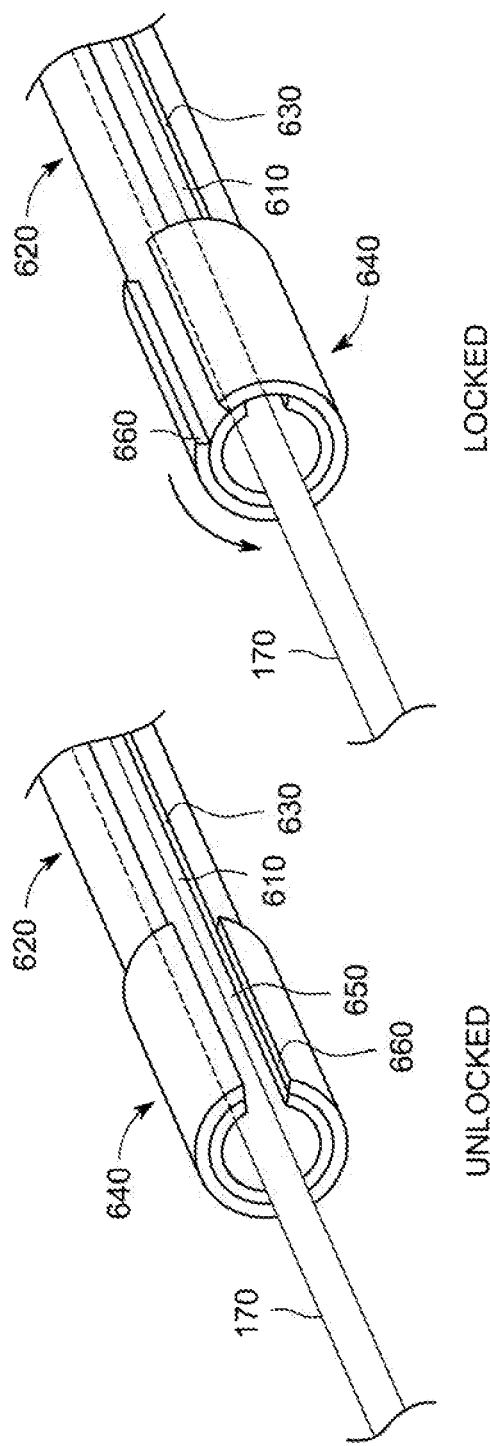

HOUSING ASSEMBLY FOR PERIODONTAL ENDOSCOPIC PROBE

CROSS-REFERENCE TO RELATED APPLICATION

The present application is related to and claims priority from provisional patent application No. 62/393,085, filed on Oct. 14, 2016, and provisional patent application No. 62/393,082, filed on Sep. 11, 2016, which are both incorporated herein by reference.

TECHNICAL FIELD

The present invention relates generally to the field of fiber optic endoscopes, and more specifically relates to a periodontal endoscopic probe.

BACKGROUND

Endoscopes may be routinely employed in various minimally-invasive and non-invasive medical procedures to assist navigation of tools being used, and to provide instant assessment of the procedure being performed. As will be appreciated, guided navigation, as well as the instant assessment, may increase effectiveness and accuracy of a procedure being performed. For example, a dental procedure for scaling and root planning (SRP) may be more effective and less painful when performed using an endoscope, and may be referred to as "VISUAL-SRP" (V-SRP). Endoscopes may allow a practitioner to view the procedure in real time, and may also allow visually guided root planning down to about a maximum of 11 mm in depth.

However, each of these procedures performed using endoscopes typically require multiple conduits and cables to be manipulated together for passage of materials (e.g., water), devices (e.g., camera), or energy (e.g., light). Various holders for managing and manipulating these multiple conduits and cables are available. However, conventional holders are difficult to use due to various challenges. For example, conventional holders may result in entangling of the cables and conduits with each other and the holder. Further, the protective sheath and fiber optics may disengage, fully or partially, from the conventional holders. Additionally, the practitioners may experience difficulty handling the conventional holder with gloved hands. These issues may also result in inadvertent damage to conduit and cables, which in turn may lead to cross-contamination. Moreover reuse of endoscopes may be a potential source of cross-contamination and undesirable infections in patients.

Therefore, there is a need in the art for a technique to protect the endoscopic probe from exposure to infectious environment and to extend the usable life of the endoscopic probe. Additionally, there is a need for a technique to provide improved handling of endoscopic probes during the procedure.

SUMMARY OF THE INVENTION

In view of the foregoing disadvantages inherent in the existing endoscopic probe sheath and existing holder, the present invention provides a novel housing assembly for an endoscopic probe and a holder for the housing assembly along with a disposable sheath.

In some embodiments, an assembly tor aiding field use of an endoscopic probe is disclosed. The assembly includes a housing assembly for an endoscopic probe and a compatible holder for the housing assembly.

In some embodiments, the housing assembly includes a tubular conduit for receiving the endoscopic probe and a plug coupled to the tubular conduit along a distal end of the tubular conduit. The tubular conduit has a flexible tubular portion, an enclosure at a distal end of the flexible tubular portion, and an optical window at a distal end of the enclosure. The tubular conduit(s) may be easily replaceable and disposable. The tubular conduit with the enclosure prevents cross contamination of the endoscopic probe, thereby extending the usable life of the endoscopic probe. The plug is adapted to couple with an inversely matching plug receiver in the compatible holder. The plug has a passage along a longitudinal axis via which the tubular conduit passes through, and, upon coupling with the inversely matching plug receiver, into the compatible holder.

In some embodiments, the compatible holder includes a handle for supporting at least a portion of the tubular conduit, a lockable sleeve, a pre-configured arm and an explorer coupled to a distal end of the pre-configured arm. The lockable sleeve is disposed coaxially at a proximal end of the handle, for securing the portion of the tubular conduit within the handle. The pre-configured arm is coupled at a distal end of the handle for facilitating the endoscopic probe assembly to explore a pre-determined quadrant of an oral cavity, the explorer includes the plug receiver and an end pan coupled to a distal end of the plug receiver. As stated above, the plug receiver is adapted to couple with the inversely matching plug of the housing assembly. The end part has an axial channel is continuation with an opening at a distal end of the plug receiver. Upon coupling the plug receiver with the inversely matching plug, the tubular conduit passes through the opening and into the axial channel of the end part.

The present invention holds significant improvements and serves as a housing assembly for an endoscopic probe and a holder for the housing assembly. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use of the present invention, a housing assembly for an endoscopic probe and a holder for the housing assembly, constructed and operative according to the teachings of the present invention.

FIG. 8A depicts the holder of FIGS. 6A and 6B with a lockable sleeve rotated with respect to the handle in an unlock position in accordance with some embodiments of the present invention.

FIG. 8B depicts the holder of FIGS. 6A and 6B with the lockable sleeve rotated with respect to the handle in a lock position in accordance with some embodiments of the present invention.

DETAILED DESCRIPTION OF THE DRAWINGS

Exemplary embodiments are described with reference to die accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

As discussed above, embodiments of the present invention relate to a housing assembly for an endoscopic probe and a compatible holder for the housing assembly. The exemplary endoscopic probe may include a fiber optic cable of about 1.2 mm diameter having about thirty thousand coherent and illumination fibers with a minimum bend radius of about 35 mm. It should be noted that the minimum bend radius may vary based on flexibility of the fiber optic cable desired.

The housing assembly may protect the endoscopic probe from exposure to infectious environment of a patient's body, thereby allowing safe reuse of the endoscopic probe. Further, the housing assembly includes a plug, which interfaces and mates with an inversely matching plug receiver of the compatible holder. The plug and the plug receiver provide a convenient and secure mechanism for coupling and uncoupling the housing assembly from the compatible holder, thereby facilitating reuse of endoscopic probes. Also, the compatible holder for the housing assembly nay be fabricated from sterilizable material and designed for structural stability so as to last reuse of about two to about six times.

Furthermore, the housing assembly may house other additional conduits such as a water and/or air channel required for performing an endoscopic procedure such as visual scaling and mot planning (V-SRP) in separate tubular conduits that interface with the plug such that there is no comingling of the water, air, and optical fibers of the endoscopic probe.

The compatible holder timber includes an arm and a handle. The arm may be pre-configured according to quadrant of oral cavity to be explored. The handle supports and secures, with a lockable sleeve, a portion the tubular conduit allowing efficient manipulation of the endoscopic probe and other conduits.

Figure 1:
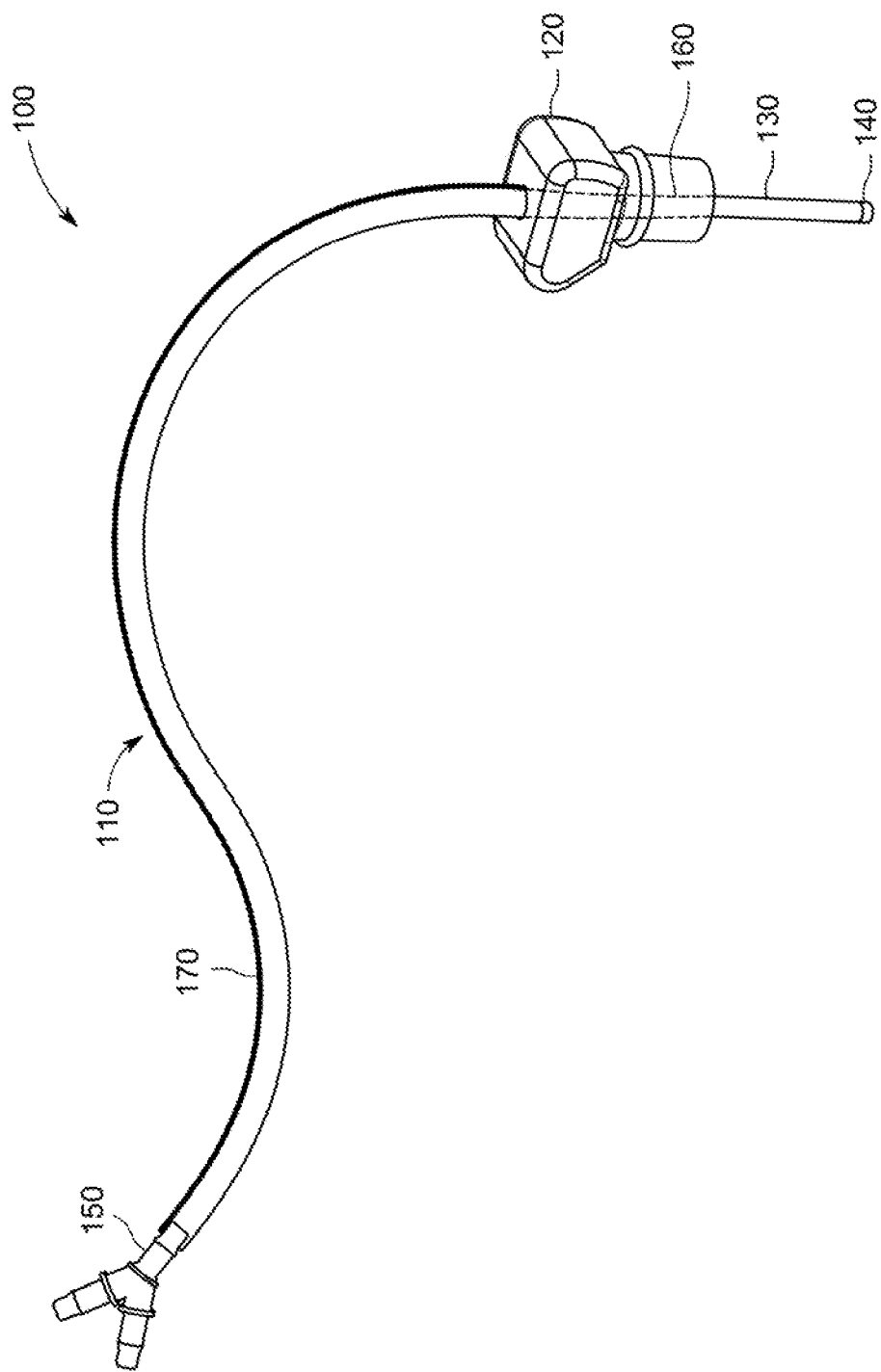
FIG. 1 is a perspective view of a housing assembly for an endoscopic probe including a connector, a tubular conduit, and a plug in accordance with some embodiments of the present invention.

Referring now to FIG. 1, a perspective view of a housing assembly 100 for an endoscopic probe is illustrated in accordance with some embodiments of the present invention. Housing assembly 100 includes a tubular conduit 110 having a connector 150 at a proximal end, and a plug 120 coupled to tubular conduit 110 along distal end of tubular conduit 110. Connector 150 couples tubular conduit 110 to an endoscopic instrument (not shown) to interface with a camera and a light source. In some embodiments, connector 150 may be a Y shaped Luer fitting. Additionally, in some embodiments, an inline micro-camera such as a CMOS, a CCD, or another microelectromechanical system (MEMS) hybrid camera that may be fed through tubular conduit may also be employed.

Figure 3A:
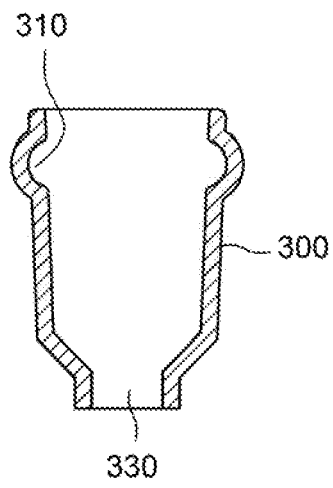
FIG. 3A is a cross-sectional view of a plug receiver including an inversely matching recess corresponding to the compressible protuberance of FIG. 2A in accordance with some embodiments of the present invention.

In some embodiments, plug 120 is adapted to couple with an inversely matching plug receiver, described in greater detail with reference to FIGS. 3A and 3B. Plug receiver is part of a compatible holder for the housing assembly, described in greater detail with reference to FIGS. 6 and 7. Compatible holder supports at least a portion of tubular conduit 110. Plug 120 includes a passage 160 along a longitudinal axis, through which a distal portion of tubular conduit 110 passes through. Further, when plug 120 couples with inversely matching plug receiver, tubular conduit 110 passes through passage 160 into compatible holder, as shown in FIG. 4. In some embodiments, plug 120 is tapered towards distal end of tubular conduit and is, for example, conical or pyramidal in shape. While tapering of plug 120 facilitates reception and coupling of plug 120 with plug receiver, various regular and irregular shapes such as cuboid, trapezium, etc., which allow coupling of plug 120 with plug receiver, are well within the scope of the present invention.

Tubular conduit 110 includes a flexible tubular portion 170, an enclosure 130 at a distal end of flexible tubular portion 170, and an optical window 140 at a distal end of enclosure 130. Flexible tubular portion 170 may be fabricated from various extruded polymeric plastics generally known in the art for use in medical equipment. The length of tubular portion 170 may vary from about a few inches to about 10 feet based on a length, or as necessary, of endoscopic probe and a portion of length of endoscopic probe, required to be housed, within tubular conduit 110. Enclosure 130 may be a rigid tubular enclosure, fabricated using for example, a suitable metal (e.g., inert metal), and hermetically sealed to flexible tubular portion 170. Optical window 140 may be a sapphire window, a metalized sapphire window, a molded plastic window, or a window fabricated from other suitable material, and hermetically sealed to enclosure 130 so as to cap a fiber optic line. As will be appreciated, the hermetic sealing prevents leakage of body fluids and other contaminants into interior of housing assembly 100 (i.e., into the interior of tubular conduit 110 housing endoscopic probe). Further, the hermetic sealing provides a stable arrangement which lasts through at least a completion of an endoscopic procedure, for example, of about 5-6 horn. Optical window 140 may be translucent or transparent, and provides, for the endoscopic visual probe, a clear bidirectional transmission of light for image formation, while protecting the endoscopic probe, housed within, from cross-contamination.

Since housing assembly 100 protects endoscopic probe from contamination and is exposed to infectious environment, preferably entire housing assembly may be fabricated from a sterilizable material, or may be fabricated from standard materials. For example, entire housing assembly 100 including tubular conduit 110 (or at least a part of tubular conduit 110) and plug 120 may be fabricated from a low temperature or gamma radiation sterilization compatible material such as ethylene oxide, or other suitable material.

Plug 120 may further include a compressible protuberance on its outer surface. Compressible protuberance is adapted to securely fit, upon application of an external pressure, into an inversely matching recess within inversely matching plug receiver. Referring now to FIGS. 2A and 3A, a cross-sectional view of plug 120 and inversely matching plug receiver 300 are illustrated in accordance with some embodiments of the present invention. As shown in FIG. 2A, outer surface of plug 120 includes ring shaped compressible protuberance 210. Ring shaped compressible protuberance 210 is adapted to securely fit, upon application of external pressure into inversely matching ring shaped recess 310 (i.e., shape matching external contour of ring shaped protuberance 210) within inversely matching plug receiver 300 shown in FIG. 3A.

Figure 2B:
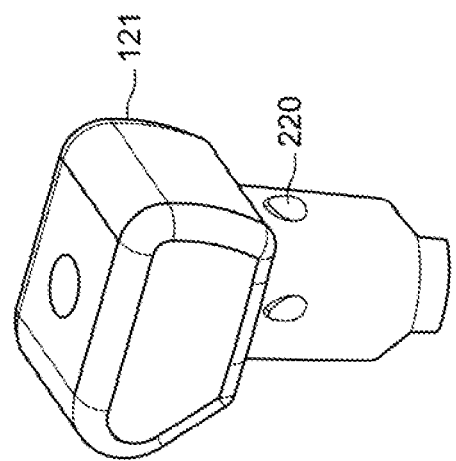
FIG. 2B is a perspective view of the plug wherein the compressible protuberance is a push button in accordance with alternate embodiments of the present invention.
Figure 2A:
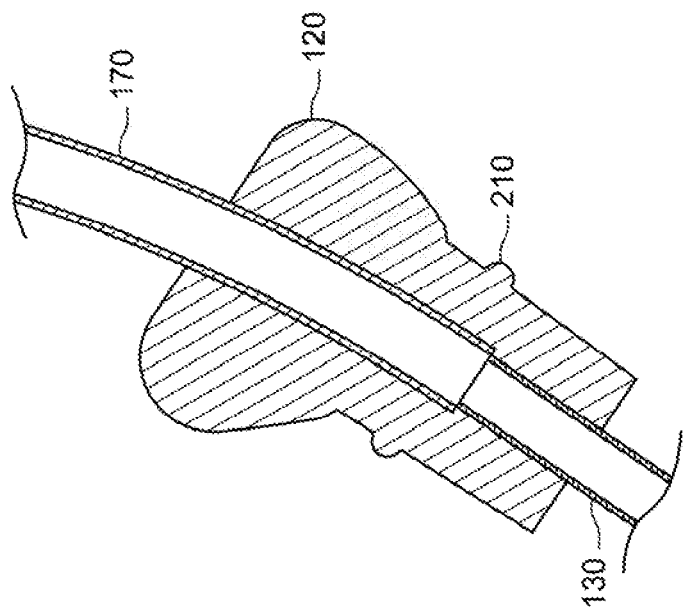
FIG. 2A is a cross-sectional view of the plug including a ring shaped compressible protuberance in accordance with some embodiments of the present invention.
Figure 3B:
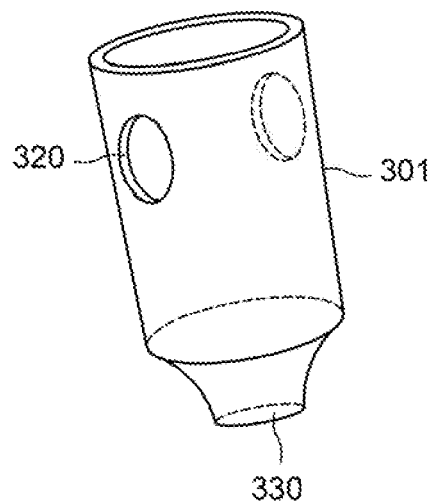
FIG. 3B is a perspective view of the plug receiver having the inversely matching recess corresponding to the push button of FIG. 2B in accordance with alternate embodiments of the present invention.
Figure 4:
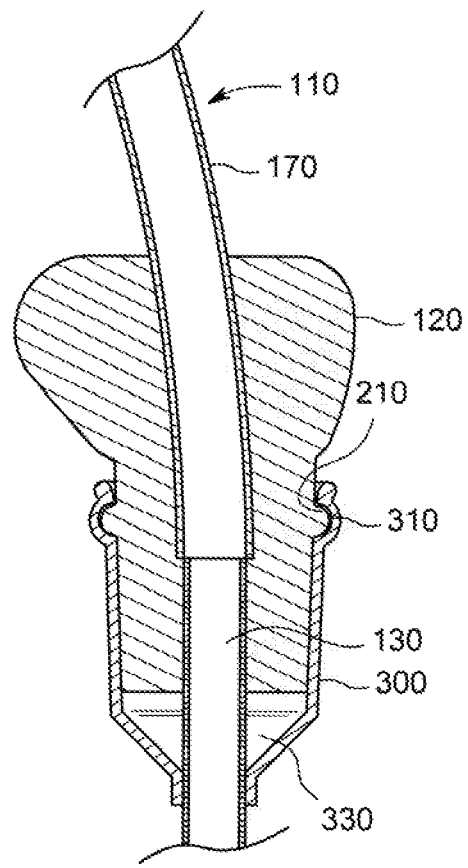
FIG. 4 is a cross-sectional view of the plug of FIG. 2A coupled with the plug receiver of FIG. 3A in accordance with some embodiments of the present invention.

Referring now to FIGS. 2B and 3B, a perspective view of alternative plug 121 and inversely matching alternative plug receiver 301 are illustrated in accordance with alternative embodiments of the present invention. As shown in FIG. 2B, outer surface of alternative plug 121 includes compressible protuberance 220 in form of multiple push buttons. In some embodiments, push buttons 220 may protrude more from outer surface at proximal part of alternative plug 121 than at distal part. Such unequal protuberance may reduce external pressure required to securely fit push buttons into inversely matching recess (i.e., shape matching external contour of push buttons) within inversely matching alternative plug receiver 301 shown in FIG. 3B. It should be noted that, in some embodiments, recess may simply be an opening 320 for push buttons (i.e., having a shape matching that of circumferential contour of push buttons). Further, as shown in FIGS. 3A and 3B, inversely matching plug receivers 300 and 301 may also include opening 330 at a distal end through which tubular conduit 110 may pass through and into compatible holder, upon coupling of plug 120 and plug receiver 300.

Referring now to FIG. 4, a cross-sectional view of plug 120 of FIG. 2A coupled with plug receiver 300 of FIG. 3A is illustrated in accordance with some embodiments of the present invention. Plug 120 may interlace with compatible holder via plug receiver 300 in a repeatable and easy to use method. Ring shaped flexible protuberance 210 effectively seals the interface between plug 120 and plug receiver 300 by securely fitting into inversely matching ring shaped recess 310. Though FIG. 4 shows plug 120 of FIG. 2A having a ring shaped compressible protuberance 210 coupled to plug receiver 300 of FIG. 3A having inversely matching ring shaped recess 310, it should be noted that alternative plug 121 of FIG. 2B may also couple with alternative plug receiver 301 of FIG. 3B having a recess or an opening 320 that inversely matches with the shape of push buttons 220 in a similar fashion. Further, as shown in FIG. 4, upon coupling of plug 120 and plug receiver 300, tubular conduit 110 that passes through passage 160 of plug 120 may pass through opening 330 of plug receiver 300 into compatible holder. Compressible protuberance 220 is shown on plug 120.

As will be appreciated, tapering plug 120 (or alternative plug 121) along with its compressible protuberance 210 (or alternatively 220) and inversely matching plug receiver 300 (or alternative receiver 301) along with its inversely matching recess or opening 310 (or alternatively 320) allow engaging housing assembly 100 with compatible holder by application of fight manual pressure by the medical practitioner without a need for any additional fastening mechanism. The intentional disengagement of the housing assembly 100 from the compatible holder may be achieved by applying manual tension by the medical practitioner in the opposite manner as above.

Figure 4C:
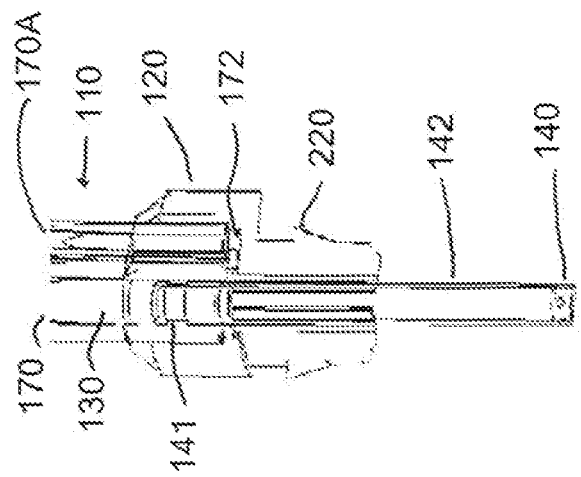
FIG. 4C is a cross-sectional view of an alternative plug of an embodiment of the present invention shown in FIG. 4A.
Figure 4B:
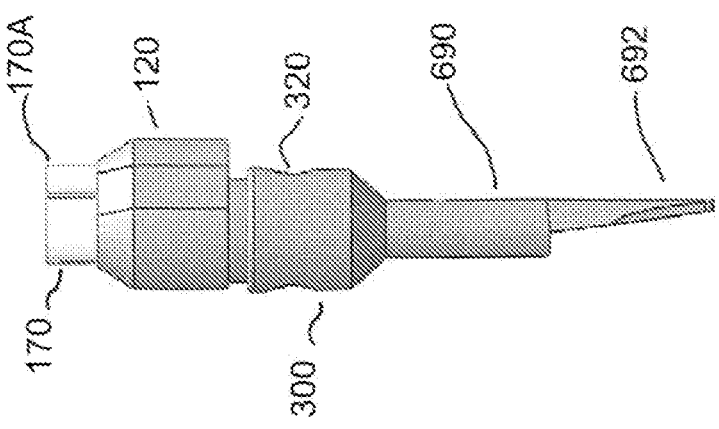
FIG. 4B is a side view of an alternative plug and receiver of an embodiment of the present invention shown in FIG. 4A.
Figure 4A:
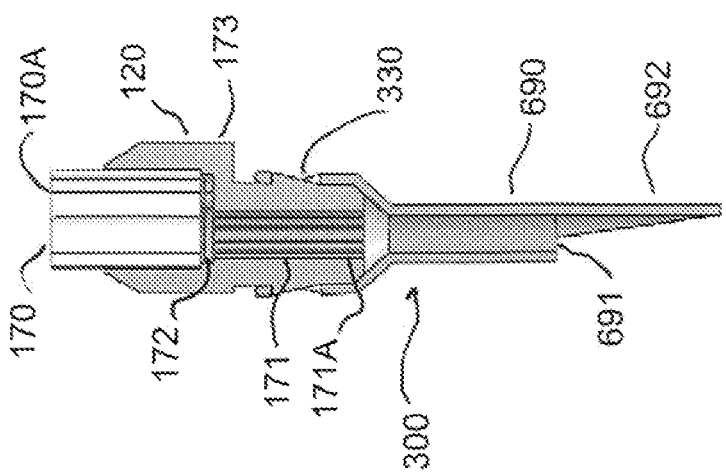
FIG. 4A is a cross-sectional view of an alternative plug and receiver of an embodiment of the present invention.

Referring to FIGS. 4A, 4B and 4C, an alternative embodiment of the plug and receiver is shown. Tubular portion 170 (such as for fiber optic scope) and first additional tubular portion 170A (such as for water source) are provided above and into plug 120. First additional tubular portion 170A terminate to water flow cavity 172 which begins to the side of enclosure 130 within channel 171 within plug 120. Water How cavity 172 surrounds lower end 171A of channel 171 to allow water to flow into plug 120 and around channel 171 housing enclosure 130 holding the fiber optic cable for camera. Plug 120 fits into opening 330 of plug receiver 300. Plug 120 may include bulging portion 173 to allow for space and structural stability of plug having bi-lumen tubing (i.e. tubing 170 and first additional tubular portion 170A). Plug fits into opening 330 of plug receiver 300. Plug receiver extends into end part 690 and opens to one side through tissue retractor 692. Enclosure 130 terminates with window 140 which may rest along receiver opening 691 along end part 690. As shown in FIG. 4C, enclosure holding optical fiber may terminate within plug and a final optic portion endoscopic shield 142, such as a metallic tube, coupled to or apart from enclosure 130 in tubular portion 170 to continue protection of fiber optic rabies at proximal joint 141. Compressible protuberance 220 is shown on plug 120.

Figure 5:
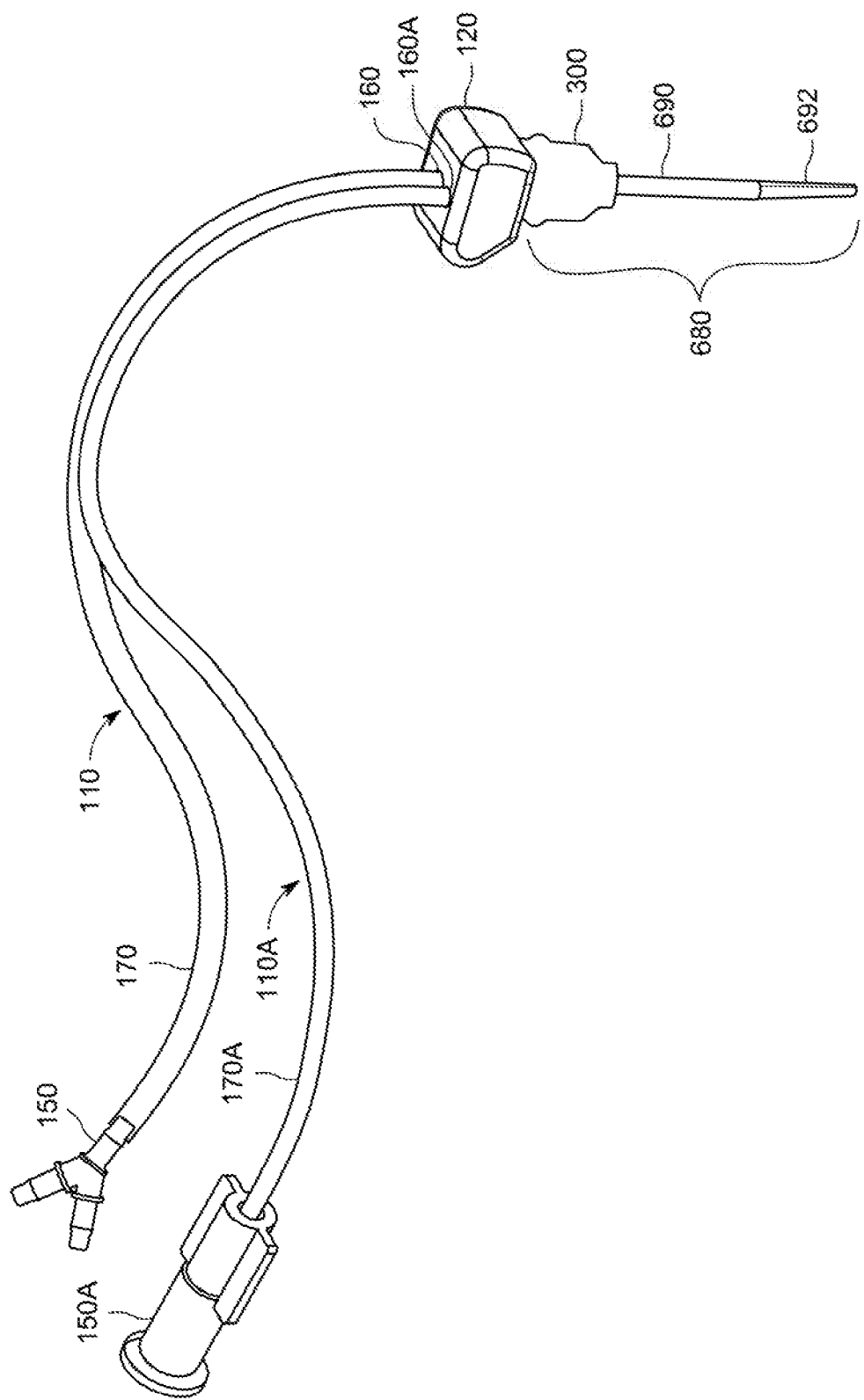
FIG. 5 is a perspective view of a housing assembly including an additional tubular conduit and a first additional passage in accordance with some embodiments of the present invention.

Referring now to FIG. 5, a perspective view of housing assembly 100 is illustrated in accordance with some embodiments of the present invention. Housing assembly 100 may include a first additional tubular conduit 110A, and a first additional passage 160A in plug 120 for the passage of first additional tubular conduit 110A through plug 120. First additional tubular conduit 110A may deliver water during the endoscopic procedure. First additional tubular conduit 110A includes a first additional tubular portion 170A and a first one-way check valve (not shown) at a distal end of first additional tubular portion 170A to prevent a backflow of water. First additional tubular conduit 110A also includes a first connector 150A at a proximal end of first additional tubular portion 170A, which couples first additional tubular conduit 110A to a water supply. Upon coupling of plug 120 with inversely matching plug receiver 300, first additional tubular conduit 110A that passes through first additional passage 160A may pass through opening 330 of plug receiver 300 into compatible holder.

Similarly, in some embodiment, housing assembly 100 may further include a second additional tubular conduit (not shown) and a second additional passage in plug 120 (not shown) for the passage of second additional tubular conduit through plug 120. For instance, second additional tubular conduit may deliver air during the endoscopic procedure. Similar to first additional tubular conduit 110A, second additional tubular conduit may include a second additional tubular portion and a second one-way check valve at a distal end of second additional tubular portion to prevent a backflow of air. Second additional tubular conduit also includes a second connector at a proximal end of second additional tubular portion, which couples second additional tubular conduit to an air supply. Upon coupling of plug 120 with inversely matching plug receiver 300, second additional tubular conduit that passes through second additional passage may pass through opening 330 of plug receiver 300 into compatible holder. In most instances, with dual tubular conduit, two separate connectors may be used (not shown). However, if a third conduit is required, i.e. camera, water and air conduit, it shows water and endoscope conduit, a Y-shaped connector 150 may be used.

As will be appreciated, additional conduits for water and/or air and additional passages in plug 120 for additional conduits, may allow delivery of water and/or air from proximal end to distal end of housing assembly 100 without comingling with endoscopic probe. Also, those skilled in the art will appreciate that while plug 120 has additional passages for each of the additional tubular conduits, plug 120 is designed to have ample material surrounding additional passages for mechanical strength and stability. However, it should be noted that, in some alternative embodiments, plug 120 may not have first additional passage 160A, and first additional tubular conduit 110A may pass through plug 120 via primary passage 160. Similarly, it should be noted that, in some alternative embodiments, plug 120 may not have second additional passage, and second additional tubular conduit may pass through plug 120 either via primary passage 160 or via first additional passage 160A.

Figure 6A:
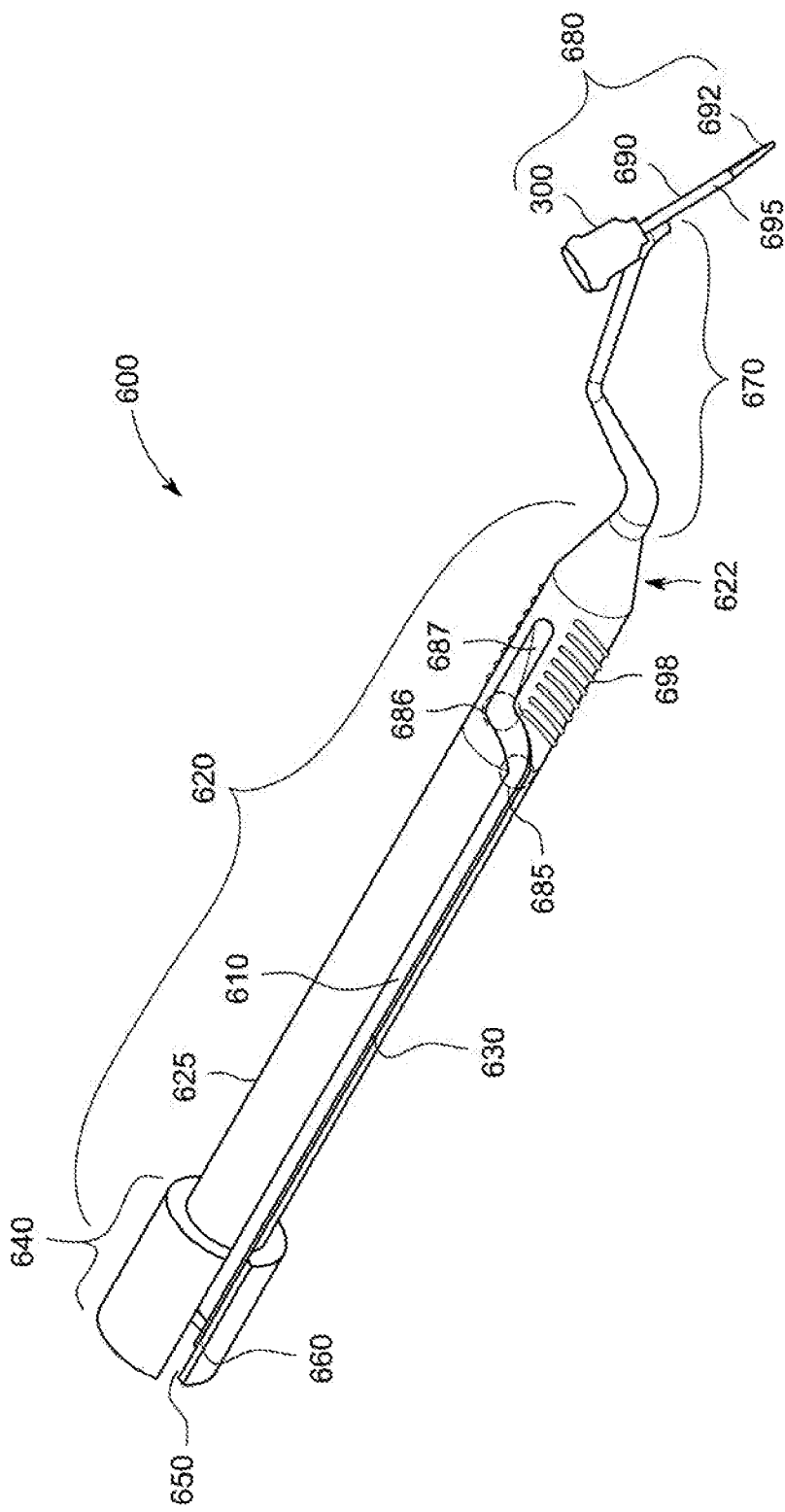
FIGS. 6A and 6B are perspective views of a holder for a housing assembly for an endoscopic probe in accordance with some embodiments of the present invention.
Figure 6B:
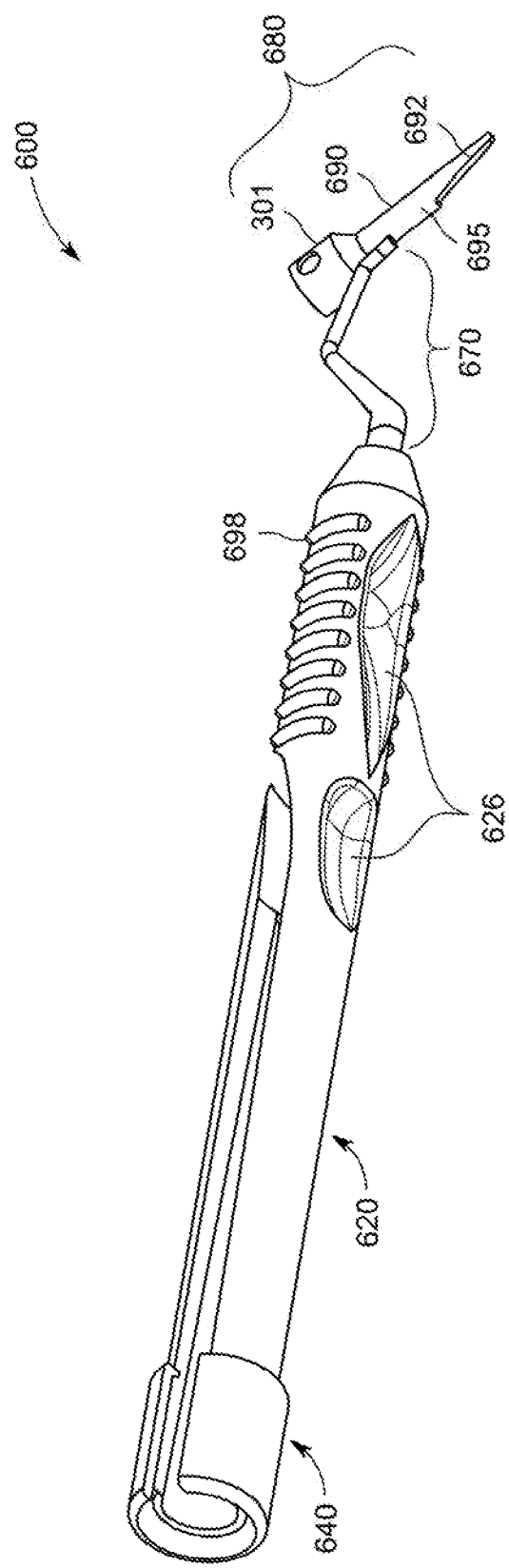

Referring now to FIGS. 6A and 6B, perspective views of a compatible holder 600 for housing assembly 100 for an endoscopic probe is illustrated in accordance with some embodiments of the present invention. Holder 600 includes a handle 620, a lockable sleeve 640, a pre-configured arm 670, and an explorer 680. Handle 620 includes a first axial channel 610 along at least a portion of handle 620, and a first slit 630 running axially along first channel 610 so as to provide an access to first channel 610. Handle 620 is adapted to receive a portion of tubular conduit of the endoscopic probe assembly (i.e., housing assembly 100 with endoscopic probe) within first channel 610 through first slit 630. In some embodiments, first slit 630 has at least one bend at a pre-determined angle. Further, in some embodiments, at least one bend is at about 45 degrees, and is towards distal end of handle 620. In the illustrated embodiment, the first slit has two bends 685 and 686, each at about 45 degrees, towards distal end of handle 620. As will be appreciated, bends 685 and 686 may prevent tubular conduit from accidentally slipping out of first channel 610 during use. Tubular conduit may exit first channel 610 after second bend 686. It should be noted that, in some embodiments, first channel 610 may have a ramp 687 for smooth exit of tubular conduit.

Lockable sleeve 640 is disposed coaxially at a proximal end of handle 620, and is adapted to further secure the portion of tubular conduit within handle 620. For example, as will be described in greater detail with reference to FIGS. 8A and 8B, lockable sleeve 640 may operate to secure the portion of tubular conduit within handle 620 such that it does not accidentally disengage from handle 620 during use. In some embodiments, lockable sleeve 640 includes a second axial channel 650 along lockable sleeve 640, and a second slit 660 running axially along second channel 650. Further, as shown in FIGS. 6A and 6B, in some embodiments, lockable sleeve 640 is disposed at least over a portion of handle 620 at the proximal end 621 of handle 620. Second slit 660 may provide access to second axial channel 650 as well as to first axial channel 610 (on the portion of handle 620 where lockable sleeve 640 overlaps with handle 620) through first slit 630. In alternate embodiments, the lockable sleeve 640 may be disposed within a portion of handle 620 (i.e., within a portion of the first channel 610) at the proximal end of handle 620. In such embodiments, second slit 660 may provide access to second axial channel 650 only. As will be appreciated, lockable sleeve 640 may be fabricated from sterilizable materials, generally known in the art, such as autoclavable plastics, metals and ceramics. Lockable sleeve may also include some indicia or differentiating aspect (e.g. color code, material, shape, number, etc.) that will identify the particular orientation of the attached arm. This color-coding can make the correct DENTAL XPLORER easily recognizable by the clinician.

Pre-configured arm 670 is coupled to handle 620 at distal end 622 of handle 620. It should be noted that, pre-configured arm 670 may be permanently coupled to distal end 622 of handle 620, or may be detachable from handle 620. Again, as will be described in greater detail with reference to FIGS. 9A-9D, in some embodiments, pre-configured arm 670 includes at least two rigid sub-arms joined by a ductile joint. Each of the at least two rigid sub-arms may be in a pre-defined direction, with respect to handle 620 and with respect to each other, so as to facilitate the practitioner to explore a pre-determined quadrant of an oral cavity with the endoscopic probe assembly.

Explorer 680 is coupled to pre-configured arm 670 at distal end of pre-configured arm 670. Explorer 680 includes plug receiver 300, and an end part 690 at a distal end of plug receiver 300. As described above, plug receiver 300 may be adapted to receive and couple with an inversely matching plug, for example plug 120, of housing assembly 100. Further, as will be described in greater detail with reference to FIG. 10, end part 690 includes a third axial channel 695 along a longitudinal axis and in continuation with opening 320 of plug receiver. When plug 120 is coupled with plug receiver 300, the tubular conduit of housing assembly 100 passes through opening 320, and into third axial channel 695. The distal tip of end part 690 is further configured to form tissue retractor 692 that is adapted to about fit between a tooth and a surrounding gum.

Additionally, in some embodiments, handle 620 may include at least we ergonomic feature or at least we grip enhancing feature. In some embodiments, diameter of handle 620 is large enough to provide ergonomic comfort to the practitioner and prevent hand fatigue, cramping, and carpel tunnel issues from prolonged and continuous handling of the compatible holder 600. Additionally, as shown in FIG. 6B, in some embodiments, ergonomic feature may include one or more portions 626 on an underside of handle 620 for resting fingers while holding compatible holder 600. Portions 626 may be indentations for finger rests. In some embodiments the indentations may correspond along the longitudinal axis as the ramp 687 to further enhance the structural strength of the handle. Further, as shown in FIGS. 6A and 6B, in some embodiments, grip enhancing feature may include knurled metal or molded grip pattern 698 disposed on an outer surface 625 of handle 620. It should be noted that molded grip pattern 698 may be formed from sterilizable and moldable materials, and disposed along entire outer surface or on select parts which are in contact with palm or fingertips of a medical practitioner's hand using holder 600. As shown in FIGS. 6A and 6B, molded grip pattern 698 may be ribs along handle 620. It should be noted that ribbed molded grip pattern 698 is for illustrative purposes only, and any geometrical, non-geometrical, coarse or fine pattern may be well within the scope of the present invention.

Figure 7:
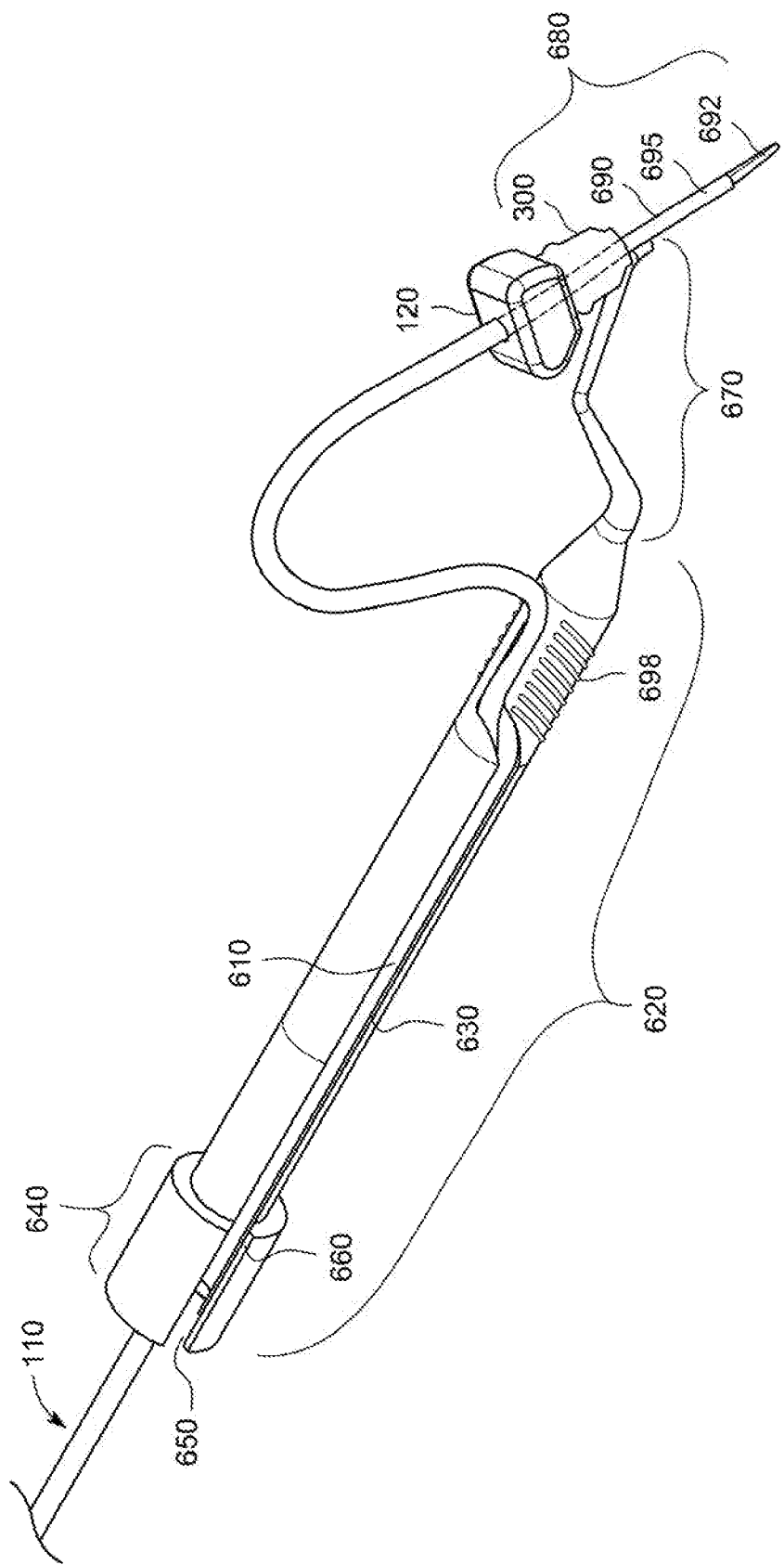
FIG. 7 is a perspective view of an assembly for aiding field use of an endoscopic probe including a housing assembly for the endoscopic probe and a holder for the housing assembly, in accordance with some embodiments of the present invention.

Referring now to FIG. 7, a perspective view of an assembly for aiding field use of an endoscopic probe including a housing assembly 100 for the endoscopic probe and a holder 600 for housing assembly 100, is illustrated in accordance with some embodiments of the present invention. A part of tubular conduit 110 of the housing assembly 100 is housed within a continuous channel formed by second axial channel 650 and first axial channel 610 of holder 600. Tubular conduit 110 exits first axial channel 610 towards distal end of the handle 620. Housing assembly 100 further couples with compatible holder 600 along distal end of housing assembly 100 via plug 120 and plug receiver 300 so as to secure distal portion of tubular conduit 110. As described above, plug 120 of housing assembly 100 couples with inversely matching plug receiver 300 of compatible holder 600 such that distal end of tubular conduit 110 (including of enclosure 130 and optical window 140) passes through opening 320 of plug receiver 300 into third axial channel 605. Such placement of optical window 140 near the end of third axial channel 695 (i.e., just above the portion where end part 690 is configured to form tissue retractor 692) allows, the practitioner performing the endoscopic procedure, an unobstructed view of the periodontal area.

Referring now to FIGS. 8A and 8B, the operation of lockable sleeve 640 with respect to handle 620 so as secure and unsecure tubular conduit 110 is illustrated in accordance with some embodiments of the present invention. FIG. 8A depicts lockable sleeve 640 rotated with respect to handle 620 in an unlock position, while FIG. 8B depicts lockable sleeve 640 rotated with respect to handle 620 in a lock position. As shown in FIG. 8A, in unlocked position, second slit 660 is aligned to first slit 630 so as to provide uninterrupted access to first channel 630. Further, as shown in FIG. 8B, in locked position, second slit 660 is misaligned with respect to first slit 630 so as to block it least a portion of first channel 630. In some embodiments, a degree of rotation of lockable sleeve 640 with respect to handle 620 may be a predetermined degree and may, for example, be about 180 degrees or about 90 degrees depending on preference, comfort of practitioners, and other manufacturing considerations. Further, in some embodiments, upon rotation of lockable sleeve 640 to lock position, lockable sleeve 640 may latch with handle 620 for preventing inadvertent unlocking during manipulation of holder 600 by the practitioner.

Figure 9A:
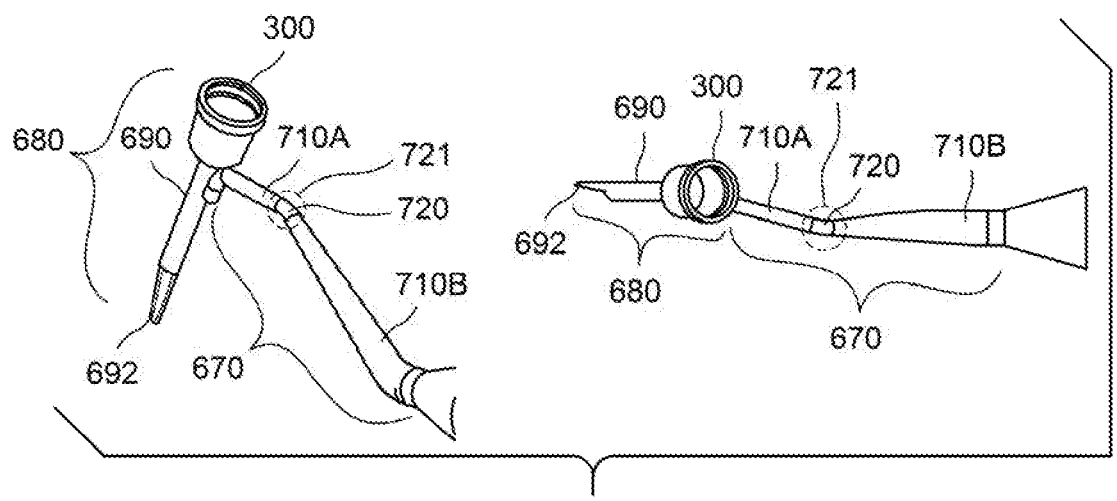
FIG. 9A through 9D depict various embodiments of a pre-configured arm of the holder of FIGS. 6A and 6B in accordance with some embodiments of the present invention.
Figure 9B:
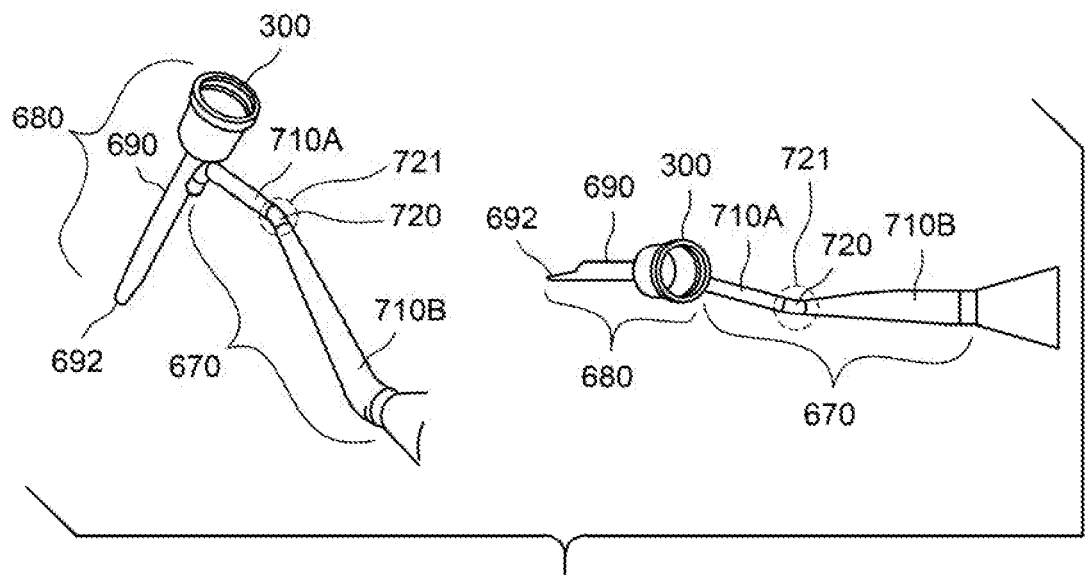
Figure 9C:
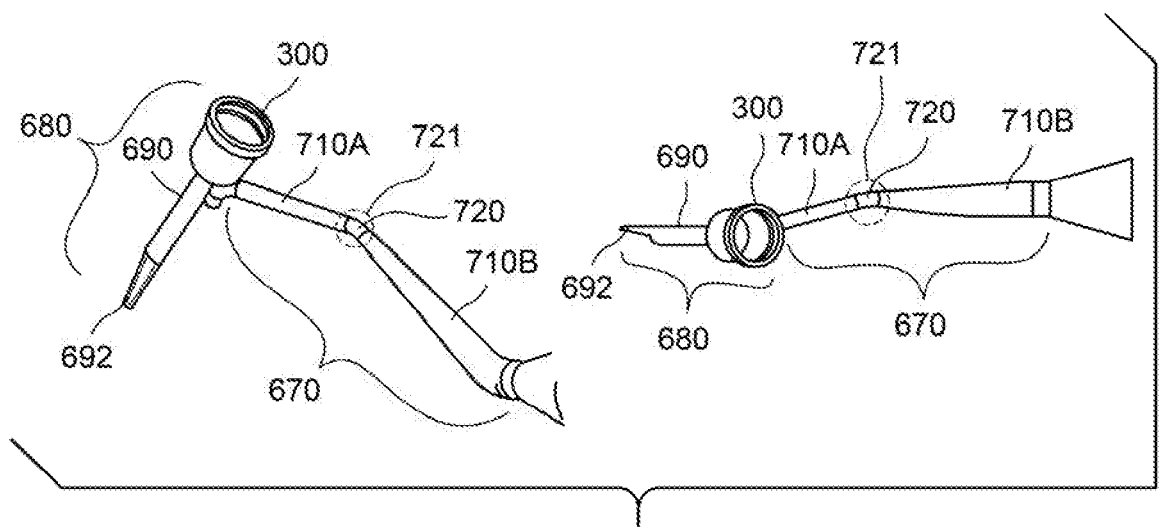
Figure 9D:
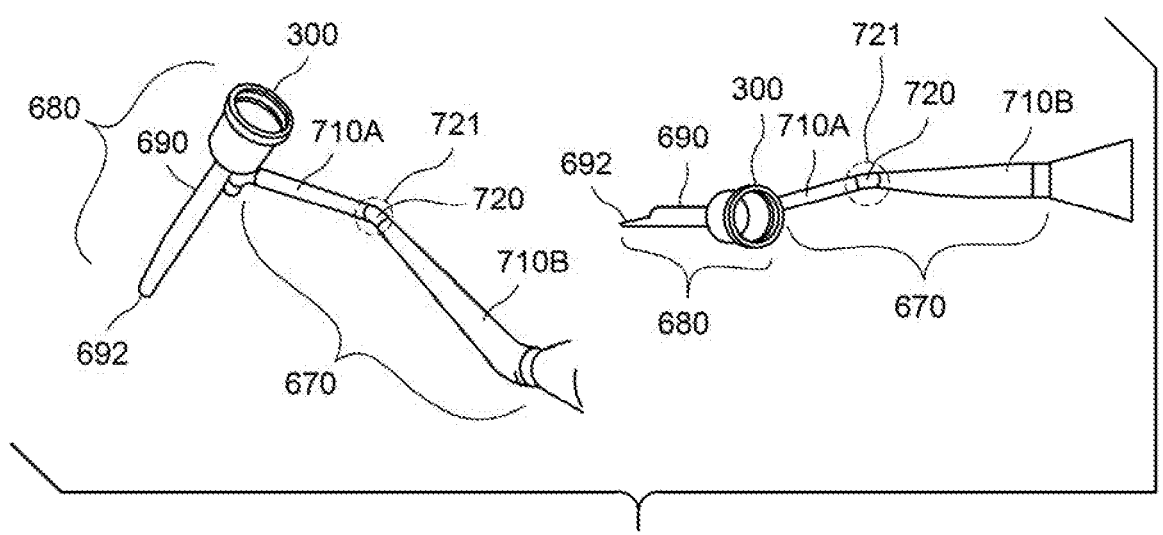

Referring now to FIGS. 9A-9D, four alternate embodiments of pre-configured arm 670 for exploring four different quadrants of the oral cavity are illustrated in accordance with aspects of the present invention. In the illustrated embodiments, pre-configured arm 670 includes two rigid sub-arms 710A and 710B joined by a ductile joint 720. Each of two rigid sub-arms 710A and 710B may be in a pre-defined direction with respect to handle 620 and with respect to each other. In some embodiments, the ductile joint may be fabricated from a steriliable and ductile metal, for example, stainless steel, aluminum, and titanium, or alloys thereof. Various pre-determined directions, corresponding to various alternate embodiments, are described in detail below. It should be noted that, in below described configurations, the first direction (i.e., left or right) refers to the direction pre-con figured arm 670 (i.e., first sub-arm 710B and second sub-arm 710A) makes with respect to handle 620 from a second bend 721, while the second direction (i.e., left or right) refers to the direction with respect to handle 620 that opening 695 in end pan 690 faces. For example, FIG. 9A shows a side view and a top view of 'left-left' configuration of pre-configured arm 670, which, for example, may be used to explore a bottom left quadrant of the oral cavity. Similarly, FIG. 9B shows a side view and a top view of 'left-right' configuration of pre-configured arm 670, which, for example, may be used to explore a bottom right quadrant of the oral cavity. Additionally, FIG. 9C shows a side view and a top view of 'right-left' configuration of pre-configured arm 670, which, for example, may be used to explore an upper left quadrant of the oral cavity. Further, FIG. 9D shows a side view and a top view of 'right-right' configuration of pre-configured arm 670, which, for example, may be used to explore an upper right quadrant of the oral cavity. Further, there may be two additional and alternate embodiments (not shown) of pre-configured arm 670, wherein the arm does not include a directional bend, so that a 'left' configuration and a 'right' configuration, would correspond to direction of the opening of the cutout of the tissue retractor 692 in the needle portion/end part 690.

Further, as will be appreciated, ductile joint may enable the practitioner to add another bend in the pre-configured arm so as to further orient arm 670 towards a particularly difficult area to access in the oral cavity. For example, a 'left-right-right' configuration and a 'right-left-right' configuration may allow exploration of extreme bottom right quadrant of the oral cavity and extreme upper left quadrant of the oral cavity respectively. It should be noted that the middle direction, in the direction combination, refers to a direction ductile portion between first sub-arm 710B and second sub-arm 710A makes with respect to handle 620. In another embodiment, the pre-configured arm 670 may include three rigid sub-arms to achieve the above stated purpose.

Figure 10:
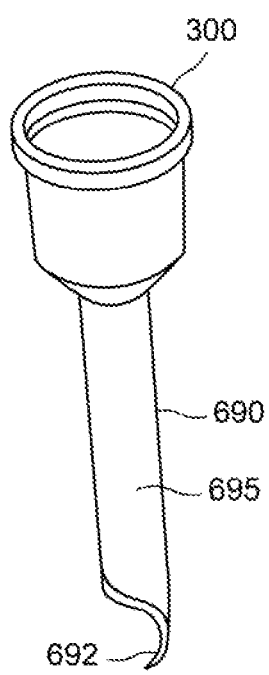
FIG. 10 depicts an explorer of the holder of FIGS. 6A and 6B, including a plug receiver, and an end part forming a tissue retractor, in accordance with some embodiments of the present invention.

Referring now to FIG. 10, a perspective view of explorer 680 is illustrated in accordance with some embodiments of the present invention. As stated above, explorer 680 includes plug receiver 300 and end part 600 such that plug receiver 300 opens into an axial channel 695 of end part 690. This allows distal end of tubular conduit to pass into end part 690 upon coupling of plug 120 with plug receiver 300. Further, as stated above, a distal tip of end part 690 is configured to form tissue retractor 692 adapted to about fit between a tooth and a surrounding gum. Tissue retractor 692 may be used by the medical practitioner performing the endoscopic procedure such as V-SRP to retract gingiva allowing visibility of the tooth root space through tire endoscopic probe.

Figure 11:
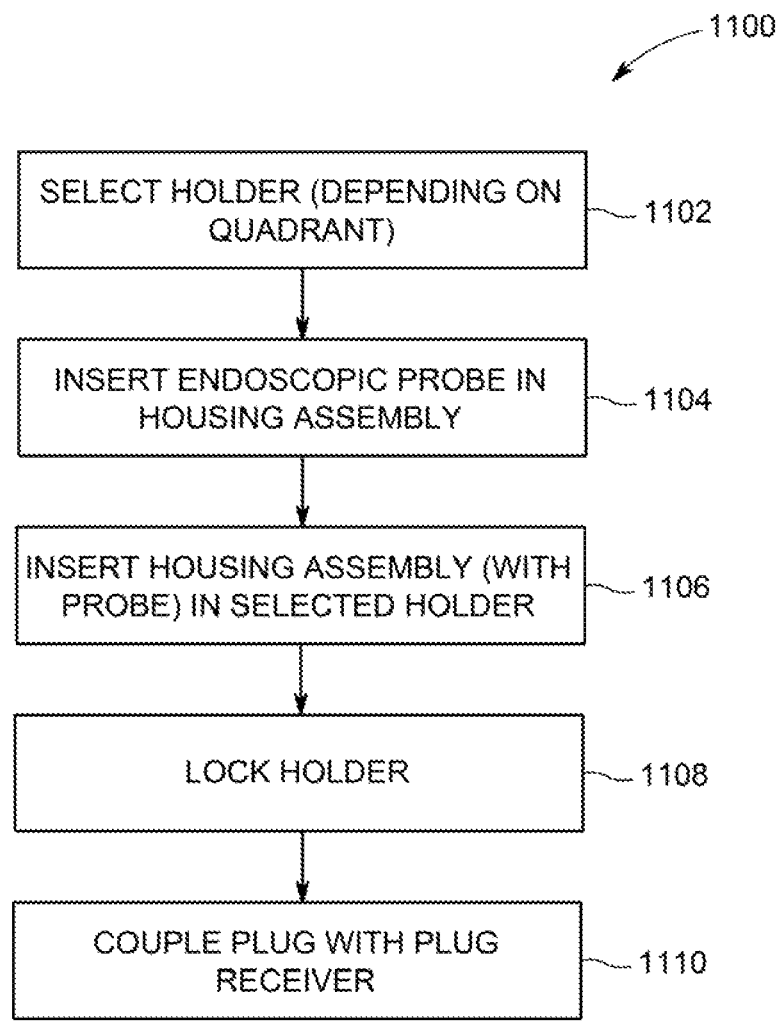
FIG. 11 is a flow chart illustrating a method of use of the assembly for aiding filed use of an endoscopic probe in accordance with embodiments of the present invention described in FIGS. 1-10.

Referring now to FIG. 11, a method of use of tire assembly for aiding filed use for an endoscopic probe is illustrated via a flowchart in accordance with embodiments of the present invention described in FIGS. 1-10. As illustrated, the method of use 1100 may include the steps of selecting a holder 600 with pre-configured arm 670 depending on quadrant of oral cavity to be explored at step 1102, inserting endoscopic probe in housing assembly 100 at step 1104, inserting housing assembly (with probe) 100 in selected holder 600 at step 1106, locking selected holder 600 using lockable sleeve 640 at step 1108, and coupling plug 120 with plug receiver 300 at step 1110.

Advantageously, housing assembly 100 may isolate endoscopic probe from exposure to infectious environment of body cavities, thereby allowing safe reuse. Further, lockable sleeve 640 secures a substantial portion of housing assembly 100 within handle 620, thereby preventing entangling, pinching, breaching and breaking of optical fibers and other conduits used for the endoscopic procedure. Furthermore, simple rotation enabled locking and unlocking as well as simple pressure enabled coupling and uncoupling allow for easy assembly and disassembly of housing assembly 100 and holder 600 with gloved hands during endoscopic procedure.

The embodiments of the invention described herein are exemplary and numerous modifications, variations and rearrangements can be readily envisioned to achieve substantially equivalent results, all of which, are intended to be embraced within the spirit and scope of the invention.

We claim:

1. An assembly for aiding field use of an endoscopic probe, the assembly comprising:
a housing assembly comprising:
a tubular conduit for receiving the endoscopic probe; and
a plug coupled to the tubular conduit along a distal end of the tubular conduit, the plug having a passage along a longitudinal axis via which the tubular conduit passes through, and a first additional passage along the longitudinal axis through which a first additional tubular conduit passes through; and
a holder for the housing assembly, the holder comprising:
a handle for supporting at least a portion of the tubular conduit;
a lockable sleeve, disposed coaxially at a proximal end of the handle, for securing the portion of the tubular conduit within the handle;
a pre-configured arm coupled to the handle at a distal end of the handle for facilitating an exploration of a pre-determined quadrant of an oral cavity with an endoscope probe assembly; and
an explorer coupled to the pre-configured arm at a distal end of the pre-configured arm, the explorer having a plug receiver and an end part at a distal end of the plug receiver, the plug receiver adapted to couple with the plug, the plug receiver having an opening along a longitudinal axis via which, upon coupling with the plug, the tubular conduit passes through and into an axial channel of the end part.

2. The assembly for aiding field use of an endoscopic probe as set forth in claim 1 wherein the plug is tapered towards the distal end of the tubular conduit.

3. The assembly for aiding field use of an endoscopic probe as set forth in claim 1 wherein the tubular conduit and/or the plug are fabricated from a low temperature sterilization-compatible material.

4. The assembly for aiding field use of an endoscopic probe as set forth in claim 1 wherein the tubular conduit further comprises a connector at a proximal end of a flexible tubular portion of said tubular conduit.

5. The assembly for aiding field use of an endoscopic probe as set forth in claim 4 wherein the connector couples the tubular conduit to an endoscopic instrument.

6. The assembly for aiding field use of an endoscopic probe as set forth in claim 4 wherein the connector is a Y shaped Luer fitting.

7. The assembly for aiding field use of an endoscopic probe as set forth in claim 1 wherein the first additional tubular conduit further comprises a first one-way check valve at a distal end of the first additional tubular conduit.

8. The assembly for aiding field use of an endoscopic probe as set forth in claim 1 wherein the first additional tubular conduit further comprises a first connector at a proximal end of the first additional tubular conduit, wherein the first connector couples the first additional tubular conduit to a water supply.

9. The assembly for aiding field use of an endoscopic probe as set forth in claim 1 further comprising a second additional tubular conduit for delivering air.

10. The assembly for aiding field use of an endoscopic probe as set forth in claim 9 wherein the second additional tubular conduit further comprises a second one-way check valve at a distal end of the second additional tubular conduit, and adapted to prevent a backflow of air.

11. The assembly for aiding field use of an endoscopic probe as set forth in claim 9 wherein the second additional tubular conduit further comprises a second connector at a proximal end of the second additional tubular conduit.

12. The assembly for aiding field use of an endoscopic probe as set forth in claim 9 wherein the plug further comprises a second additional passage along the longitudinal axis through which the second additional tubular conduit passes through.

13. The assembly for aiding field use of an endoscopic probe as set forth in claim 1 further comprising an optical window at the distal end of said tubular conduit.

14. The assembly for aiding field use of an endoscopic probe as set forth in claim 13 wherein the optical window is hermetically sealed to said tubular conduit.

15. The assembly for aiding field use of an endoscopic probe as set forth in claim 13 wherein the optical window is comprised of a sapphire, metallic, or a molded plastic.

16. The assembly for aiding field use of an endoscopic probe as set forth in claim 1 wherein said handle comprises an axial slit.

17. The assembly for aiding field use of an endoscopic probe as set forth in claim 1 wherein the pre-configured arm is detachable from the handle.

18. The assembly for aiding field use of an endoscopic probe as set forth in claim 1 wherein the pre-configured arm comprises at least two rigid sub-arms.

19. The assembly for aiding field use of an endoscopic probe as set forth in claim 18 wherein the at least two rigid sub-arms are in one of a left, a right, a left-left, a left-right, a right-left, and a right-right configuration.

* * * * *